(12) United States Patent
Marchetti et al.

(10) Patent No.: US 11,123,755 B2
(45) Date of Patent: Sep. 21, 2021

(54) DIFFUSER OF ACTIVE AGENTS SUCH AS INSECTICIDES, PERFUMES, DETERGENTS OR DISINFECTANTS, AND MANUFACTURING PROCESS THEREOF

(71) Applicant: ZOBELE HOLDING S.P.A., Trento (IT)

(72) Inventors: Fabio Marchetti, Trento (IT); Stefano Deflorian, Trento (IT); Franco Zobele, Trento (IT)

(73) Assignee: ZOBELE HOLDING S.P.A., Trento (IT)

( * ) Notice: Subject to any disclaimer, the term of this patent is extended or adjusted under 35 U.S.C. 154(b) by 286 days.

(21) Appl. No.: 16/066,880

(22) PCT Filed: Dec. 28, 2016

(86) PCT No.: PCT/IB2016/058034
§ 371 (c)(1),
(2) Date: Jun. 28, 2018

(87) PCT Pub. No.: WO2017/115288
PCT Pub. Date: Jul. 6, 2017

(65) Prior Publication Data
US 2019/0001349 A1 Jan. 3, 2019

(30) Foreign Application Priority Data
Dec. 31, 2015 (IT) .......................... 102015000089512

(51) Int. Cl.
*A61L 9/04* (2006.01)
*A61L 9/12* (2006.01)
(Continued)

(52) U.S. Cl.
CPC ................ *B05B 1/00* (2013.01); *A61L 9/042* (2013.01); *A61L 9/048* (2013.01); *A61L 9/12* (2013.01);
(Continued)

(58) Field of Classification Search
CPC . A61L 9/037; A61L 9/12; A61L 9/127; A61L 2209/131; A01M 1/2044;
(Continued)

(56) References Cited

U.S. PATENT DOCUMENTS 3,358,821 A * 12/1967 Weyenberg ............ B65D 75/42
383/37
4,145,001 A * 3/1979 Weyenberg ............... A61L 9/12
239/56
(Continued)

FOREIGN PATENT DOCUMENTS

WO 94/27646 A1 12/1994

OTHER PUBLICATIONS

International Search Report, dated May 23, 2017, from corresponding PCT/IB2016/058034 application.

*Primary Examiner* — Joseph A Greenlund
(74) *Attorney, Agent, or Firm* — Nixon & Vanderhye (57) ABSTRACT

Diffuser of an active liquid agent, for the treatment of a fluid environment, be it at the gaseous or liquid state, of the type including a container (1) of the active agent, closed by grid element apt to maintain in position the active agent and to allow the emanation of fluids of the same, the grid element being covered by a barrier film, peelable at the time of the first use to make operative the grid element, wherein the container (1) is closed by a single multilayer film (2, 3*a*, 3*b*) including at least one external barrier layer (3*a*) and at least another inner sealing layer (2) apt to maintain in position the active agent and to form the grid element, at the time of the
(Continued)

first use of the container, following the simultaneous removal of the barrier film and of predefined portions of the sealing layer.

19 Claims, 5 Drawing Sheets

(51) Int. Cl.
| | | |
|---|---|---|
| B05B 1/00 | (2006.01) | |
| B32B 7/06 | (2019.01) | |
| B32B 15/085 | (2006.01) | |
| B32B 15/20 | (2006.01) | |
| B32B 27/08 | (2006.01) | |
| B32B 27/32 | (2006.01) | |
| B32B 3/26 | (2006.01) | |
| B32B 3/30 | (2006.01) | |
| B32B 15/09 | (2006.01) | |
| B32B 27/36 | (2006.01) | |

(52) U.S. Cl.
CPC .............. *A61L 9/127* (2013.01); *B32B 3/266* (2013.01); *B32B 3/30* (2013.01); *B32B 7/06* (2013.01); *B32B 15/085* (2013.01); *B32B 15/09* (2013.01); *B32B 15/20* (2013.01); *B32B 27/08* (2013.01); *B32B 27/32* (2013.01); *B32B 27/36* (2013.01); *A61L 2209/133* (2013.01); *B32B 2250/03* (2013.01); *B32B 2250/04* (2013.01); *B32B 2307/31* (2013.01); *B32B 2307/724* (2013.01); *B32B 2307/7242* (2013.01); *B32B 2307/7248* (2013.01); *B32B 2307/7265* (2013.01); *B32B 2307/748* (2013.01)

(58) Field of Classification Search
CPC ................. A01M 1/2055; B32B 27/08; B32B 2307/724; B65D 75/5855
USPC ................................................ 239/34, 55–58
See application file for complete search history.

(56) References Cited

U.S. PATENT DOCUMENTS

| | | | | |
|---|---|---|---|---|
| 4,157,787 A * | 6/1979 | Schwartz | A61L 9/12 | 239/56 |
| 4,160,335 A * | 7/1979 | Von Kohorn | B32B 1/02 | 43/131 |
| 4,285,468 A * | 8/1981 | Hyman | A01M 1/2044 | 239/55 |
| 4,356,969 A * | 11/1982 | Obermayer | A01M 1/2044 | 239/56 |
| 4,529,125 A * | 7/1985 | Sullivan | A61L 9/12 | 239/56 |
| 4,634,614 A * | 1/1987 | Holzner | A61L 9/042 | 428/34.2 |
| 4,753,389 A * | 6/1988 | Davis | A61L 9/01 | 239/56 |
| 4,767,016 A * | 8/1988 | Cook, Jr. | B65D 51/20 | 215/230 |
| 4,804,142 A * | 2/1989 | Riley | A01M 29/12 | 239/56 |
| 4,955,945 A * | 9/1990 | Weick | A61M 15/0011 | 128/203.12 |
| 5,372,303 A * | 12/1994 | Paul | A61L 9/037 | 239/56 |
| 5,395,047 A * | 3/1995 | Pendergrass, Jr. | A61L 9/12 | 239/34 |
| 5,439,100 A * | 8/1995 | Gordon | A61L 9/12 | 206/204 |
| 5,591,146 A * | 1/1997 | Hasse | A61F 13/8405 | 604/359 |
| 5,782,409 A * | 7/1998 | Paul | A61L 9/12 | 239/56 |
| 5,804,264 A * | 9/1998 | Bowen | A61L 9/12 | 428/35.2 |
| 5,845,847 A * | 12/1998 | Martin | A61L 9/12 | 239/58 |
| 5,919,547 A * | 7/1999 | Kocher | B32B 7/06 | 428/138 |
| 6,109,537 A * | 8/2000 | Heath | A61L 9/12 | 239/51.5 |
| 6,227,458 B1 * | 5/2001 | Dever | A43B 1/0045 | 239/36 |
| 6,248,380 B1 * | 6/2001 | Kocher | B32B 7/06 | 206/484 |
| 6,670,023 B2 * | 12/2003 | Mueller | B32B 7/06 | 206/459.5 |
| 8,439,280 B2 * | 5/2013 | Marchetti | B05B 17/0646 | 239/102.2 |
| 8,567,693 B2 * | 10/2013 | Roreger | A61L 9/042 | 239/53 |
| 8,617,677 B2 * | 12/2013 | Trouilhet | B32B 27/32 | 428/35.7 |
| 8,677,679 B2 * | 3/2014 | Black | A01M 1/2033 | 43/123 |
| 8,740,110 B2 * | 6/2014 | Gruenbacher | A61L 9/127 | 239/34 |
| 10,264,777 B2 * | 4/2019 | Zhang | A01M 1/02 | |
| 10,478,516 B1 * | 11/2019 | Huang | A01M 1/2055 | |
| 2001/0000235 A1 * | 4/2001 | Bowen | B32B 27/322 | 428/500 |
| 2002/0131888 A1 * | 9/2002 | Zobele | A61L 9/02 | 422/5 |
| 2003/0168521 A1 * | 9/2003 | Skalitzky | A61L 9/03 | 239/57 |
| 2004/0076553 A1 * | 4/2004 | Zobele | A01M 1/2044 | 422/123 |
| 2006/0010840 A1 * | 1/2006 | Ashiya | A61L 9/12 | 53/450 |
| 2009/0302128 A1 * | 12/2009 | Zobele | A61L 9/12 | 239/59 |
| 2010/0270392 A1 * | 10/2010 | Trent | A01M 1/2077 | 239/55 |
| 2012/0048964 A1 * | 3/2012 | Willed | A01M 1/2055 | 239/57 |
| 2012/0280055 A1 * | 11/2012 | Schneidmiller | A01M 29/12 | 239/6 |
| 2013/0175355 A1 * | 7/2013 | Lackey | A61L 9/12 | 239/57 |
| 2014/0048614 A1 * | 2/2014 | Santini | B32B 27/306 | 239/6 |
| 2014/0166774 A1 * | 6/2014 | Morhain | A01M 1/2044 | 239/34 |
| 2014/0209698 A1 * | 7/2014 | Olchovy | A01M 1/2055 | 239/6 |
| 2014/0209700 A1 * | 7/2014 | Olchovy | A61L 9/12 | 239/34 |
| 2014/0239079 A1 * | 8/2014 | Wolf | A61L 9/12 | 239/6 |
| 2014/0239088 A1 * | 8/2014 | Wolf | A61L 9/12 | 239/58 |
| 2018/0064839 A1 * | 3/2018 | Hsiao | A61L 9/12 | |
| 2018/0161470 A1 * | 6/2018 | Zobele | A61L 9/12 | |
| 2019/0001349 A1 * | 1/2019 | Marchetti | B32B 7/06 | |
| 2020/0023093 A1 * | 1/2020 | Sordo | A01M 1/2044 | |

\* cited by examiner

DIFFUSER OF ACTIVE AGENTS SUCH AS INSECTICIDES, PERFUMES, DETERGENTS OR DISINFECTANTS, AND MANUFACTURING PROCESS THEREOF

FIELD OF THE INVENTION

The present invention relates to a diffuser of active liquid agents—such as for example insecticides, perfumes, detergents or disinfectants—for the treatment of a surrounding fluid environment, be it at the gaseous or liquid state, that are imbued in a solid or gel-like support. Such a diffuser is of the type having at least one wall closed by a containment grid of the solid or gel-like support of the active agent and by a removable external barrier film, impermeable to fluids, which covers the active agent and the grid during the diffuser storage and transport steps. The invention also relates to a manufacturing process of such a diffuser.

PRIOR STATE OF THE ART

Devices consisting of a box-shaped container of the above indicated type are well known in the art; they are used to make up a large supply of active agents which—as it happens for many products treating a liquid or gaseous environment—are sufficiently soluble or evaporable in the fluid of which said environment consist, to cause a slow release of the active agent towards the environment, through said grid. Said emission may possibly be accelerated with the aid of an additional heating of the fluid flowing around the device.

In known diffusers, the grid has the following functions:
retaining the active agent support in a correct and stable position inside the diffuser;
avoiding the contact between the active agent and the hands or other parts of the user's body;
allowing the emission of the active agent towards the surrounding environment, once the external barrier film has been removed;
and is made of a solid material, preferably an injection-moulded plastic material.

As already said, in order to prevent the diffusion of the active agent from starting before the first use of the diffuser by the user, an external barrier film impermeable to fluids is applied onto the external side of the grid. A stable adhesion between the grid material and the external barrier film is obtained by means of an adhesive or by thermal welding. The adhesion strength between these two elements must be sufficiently high to prevent the active agent from leaking between the grid and the external barrier film or the external barrier film from accidentally detaching during transport, storage and sale, and yet still sufficiently low to allow the user to remove the external barrier film at the time of use without excessive effort.

Normally, the remaining surface of the diffuser body consists of continuous walls of plastic material, which the active agent cannot pass through; it is possible to provide a second grid also on the opposite side of the diffuser body, in order to have a higher overall emission rate of the active agent.

The following are mentioned among the drawbacks of the existing solutions of this type:
as said above, the grids are usually made of injection-moulded plastic material; this involves the production of a separate element in addition to the container, which has its own cost of production and an additional cost for assembling it on of the diffuser body, before the application of the external barrier film;
the application process of the external barrier film on the grid has a certain complexity (label positioning, non-flatness of the injection-moulded piece, positioning differences between pieces, etc.) possibly resulting in an impairment of the final quality of the manufactured item;
the active substance may interact with the adhesive layer during its application or hinder the thermal welding process thus leading to an early separation of the external barrier film from the grid.

SUMMARY OF THE INVENTION

The object of the invention is therefore to provide a structure for a diffuser that:
overcomes the above mentioned drawbacks in the manufacturing process of the known-type diffusers, by reducing the number of pieces to be manufactured and consequently simplifying the assembly step;
provides better performances with reference to the adhesion stability of the external barrier film and, consequently, to any possible active agent leaking;
allows the user an easier start-up operation of the activation function of the diffuser; and, finally,
exhibits a reduced manufacturing cost compared to diffusers of the known art.

This multiple object is fully achieved by a diffuser of an active liquid agent, for the treatment of a fluid environment, be it at the gaseous or liquid state, of the type comprising a container (1) of the active agent, closed by grid means apt to retaining in position said active agent and to allow the emanation of fluids of the same, said grid means being covered by a barrier film, peelable at the time of the first use to make operative said grid means, wherein said container (1) is closed by a single multilayer film (2, 3a, 3b) comprising at least one external barrier layer (3a) and at least another inner sealing layer (2) apt to retaining in position said active agent and to form said grid means, at the time of the first use of the container, following the removal of said barrier film and of predefined portions (4) of said sealing layer (2).

Other preferred features of the invention are disclosed in the dependent claims.

BRIEF DESCRIPTION OF THE DRAWINGS

Further features and advantages of the invention will anyhow be more evident from the following detailed description of some preferred embodiments of the same, provided as a mere and non-limiting example and illustrated in the attached drawings, wherein.

DETAILED DESCRIPTION OF PREFERRED EMBODIMENTS OF THE INVENTION

Figure 1:
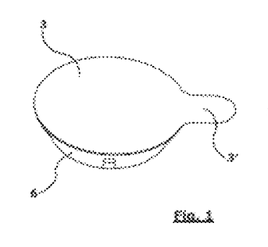
FIG. 1 is a perspective view of a diffuser according to a first embodiment of the invention, in the closed configuration prior to use.
Figure 2:
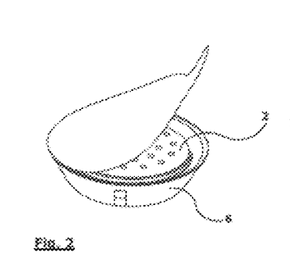
FIG. 2 is a view similar to FIG. 1, taken while removing, by peeling it, part of the multilayer film which closes the diffuser.
Figure 3:
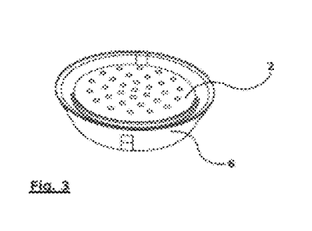
FIG. 3 is a perspective view similar to FIG. 2, with part of said multilayer film completely removed.

As outlined in FIGS. 1 to 3, a diffuser according to the present invention consists of a container body 1 for the active liquid agent, and a multilayer film 3, which is welded to the body 1. The active liquid agent can be totally imbued in a solid or gel-like support, or it can be contained in a reservoir which is separated from the multilayer film by a solid support apt to be imbued with the active liquid agent and which therefore acts as a wick. In any case, thus, the multilayer film 3 is in contact with a solid internally, and in contact with the environmental fluid, in the gaseous or liquid state, externally.

According to the present invention, the multilayer film 3 is directly applied on the edge of the container 1 and is able to serve both as a grid and an external barrier layer, which functions, in known diffusers, were performed by two separate components. In order to achieve this innovative and striking result, the closing multilayer film consists of the following coupled layers:

an inner sealing layer 2, apt to maintain in stable position the solid or gel-like support of the active agent, which has an inner structure of incisions which run through the entire thickness of said layer, according to a predefined pattern;

an external barrier layer 3a, apt to prevent the active agent from leaking outwards;

an intermediate release layer 3b, apt to facilitate the detachment by peeling between said intermediate release layer 3b and the inner layer 2, when a sufficient traction effort is imparted to the external barrier layer 3a through its projecting tab 3'.

Optionally, a further layer (not shown in the figures) can be applied on the external barrier layer 3a, the whole to confer to the same additional chemical and/or mechanical protection.

The inner layer 2 of the multilayer film of the present invention can be defined as a layer "provided with an inner structure of incisions" or more briefly as a "structured" layer, because this layer is cut throughout its depth according to one or more closed lines of a desired shape, which delimit the perimeter of incision areas 4 which are therefore no longer laterally connected to the remaining part of the film 2. Thus, when the peelable part of the multilayer film 3—i.e. both the layers 3a and 3b—are removed, through the tearing action on tab 3', the incision areas 4 of the inner sealing layer 2 remain adhering to the overlying intermediate release layer 3b and they are removed with it, while on the free surface of the container 1 remains only the part 5 of the inner sealing layer 2, freed from the incision areas 4, therefore having a plurality of orifices 6. In this way, this part 5 of the inner sealing layer 2 is therefore able to perform the same functions as seen above for the grid of the known-art diffusers, i.e. keeping the solid or gel-like active agent support in position, while allowing the emission of the agent to the surrounding fluid environment, be it at a gaseous or liquid state, in the form of vapours or solution, respectively.

In order to obtain that the incision areas 4 of the inner sealing layer 2 remain adhering to the layer 3b while the portion 5 of inner sealing layer 2 remains adhering to the edge of the container, it is sufficient to operate as follows: on one hand, care is taken to secure the contour of the multilayer film, and therefore of its inner sealing layer 2, to the upper flange edge of the container 1 in a particularly accurate manner, for example by thermal welding, so that this fixing offers a great mechanical strength in terms of detachment from the container 1. On the other hand, a structure of incision areas is formed in the inner sealing layer 2 with the following conformation: the incision areas are delimited by a closed perimeter; the incisions go through the entire thickness of the inner sealing layer 2; the incision areas preferably do not intersect; and, preferably, the incision areas do not extend in the perimeter area of the inner sealing layer 2, so that the remaining part 5 of this inner sealing layer, after removal of said incision areas 4, still has a sufficient mechanical strength.

In this way, when the external barrier layer 3a and the intermediate release layer 3b of the multilayer film are removed by peeling, by pulling the tab 3', the perimeter edge of the inner sealing layer 2—which, as said, is firmly fixed to the flange edge of the container 1—together with the remaining portion 5 of the same inner sealing layer, remains adhering to the container 1; while the incision areas 4—which, as a result of said incisions, are no longer joined laterally to the remaining part of the sealing layer 2—will be removed thanks to their adhesion to the intermediate release layer 3b. The depth of said closed-perimeter incision lines is not necessarily strictly limited to the inner sealing layer 2, but it can extend further within the intermediate release layer 3b and possibly also affect the entire thickness of this intermediate release layer 3b, thus making the adjustment of the cutting depth during the manufacturing process less critical. Obviously, it is preferable that the cutting action not to reach the external barrier layer 3a, typically of aluminium, so as not to risk damaging the integrity of this external barrier layer, which action could reduce the overall barrier properties of the multilayer film of the present invention.

A cutting process for manufacturing such a multilayer film according to the invention is the one which provides for the use of a standard Form Fill Seal machine type, commonly used in the flexible packaging industry, and to perform the cutting operation of the inner sealing layer 2 in a stage preceding the sealing closure of the container 1. In this way, it is possible to obtain more easily a good positioning of the different incision areas 4 with respect to the inside of the cavity of the container 1.

The incision can be done mechanically, with blades designed to reach a certain depth inside the inner sealing layer 2, and optionally the intermediate release layer 3b. Alternatively, the cut can be made using a thermal-action knife (thermocutter) which can dissolve the plastic material layer 2. Preferably, the cut will be rather performed using laser cutting technology, where the applied power control can be performed in a very precise way, so as to achieve a certain desired cutting depth. This latter process is particularly preferred because it does not involve specific mechanical equipment according to the cutting pattern, so that different patterns of incision areas 4 may be obtained with the same cutting machine, thus allowing to manufacture products with different features and performances just by appropriately programming said cutting machine. It is quite clear that the distribution and the geometry of the incision areas 4 will be defined from time to time according to the specific application requirements.

In the following, the diffuser of active agents of the present invention will be described with reference to some specific examples of application.

Example 1—Container of Active Agents on a Solid Support (FIGS. 1-3)

The container 1 is made from a PE plastic material, 1.5 mm thick, injection moulded in the shape of a circular cup with a diameter of 50 mm.

Inside this container 1 a cellulose pad is placed, impregnated with an active liquid substance (perfume, disinfectant, insecticide, etc.) having similar dimensions to the inner diameter of the circular cup, so as to find a stable position within the container.

A multilayer film according to the invention is positioned on top of the container and heat-sealed on the contour flange of the cup of the container 1.

Figure 4A:
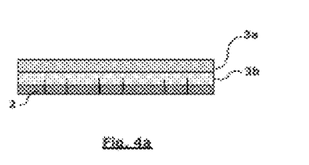
FIGS. 4a and 4b are schematic, greatly enlarged, cross-sectional views, of the whole multilayer film (FIG. 1) and of the portion of said multilayer film that remains adhering to the container after the opening of the diffuser device (FIG. 3), respectively.

The multilayer film consists of, from inside outwards, a PE inner sealing layer 2, a PP intermediate release layer 3b, an aluminium external barrier layer 3a, and by a further external PET protection layer.

The PE inner sealing layer 2 is cut according to multiple incision areas 4, having a circular geometrical shape with a diameter of about 2 mm. Their position is distributed in a regular manner in correspondence with the central area of the container 1.

Figure 4B:
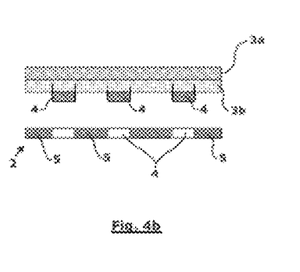

When the aluminium external barrier layer 3a is removed, together with the PP intermediate release layer 3b, the PE material corresponding to the above multiple incision areas 4, formed in the inner sealing layer 2, is simultaneously removed, creating round holes 6 in said PE inner sealing layer 2. Through these holes 6, the active substance imbued in the pad—in the form of vapour or solution, depending on whether the container 1 is positioned in a gaseous or liquid environment—can be emanated, while the pad itself is kept in position and inhibited from contact with the user from the remaining portion 5 of the PE inner sealing layer 2.

Figure 5:
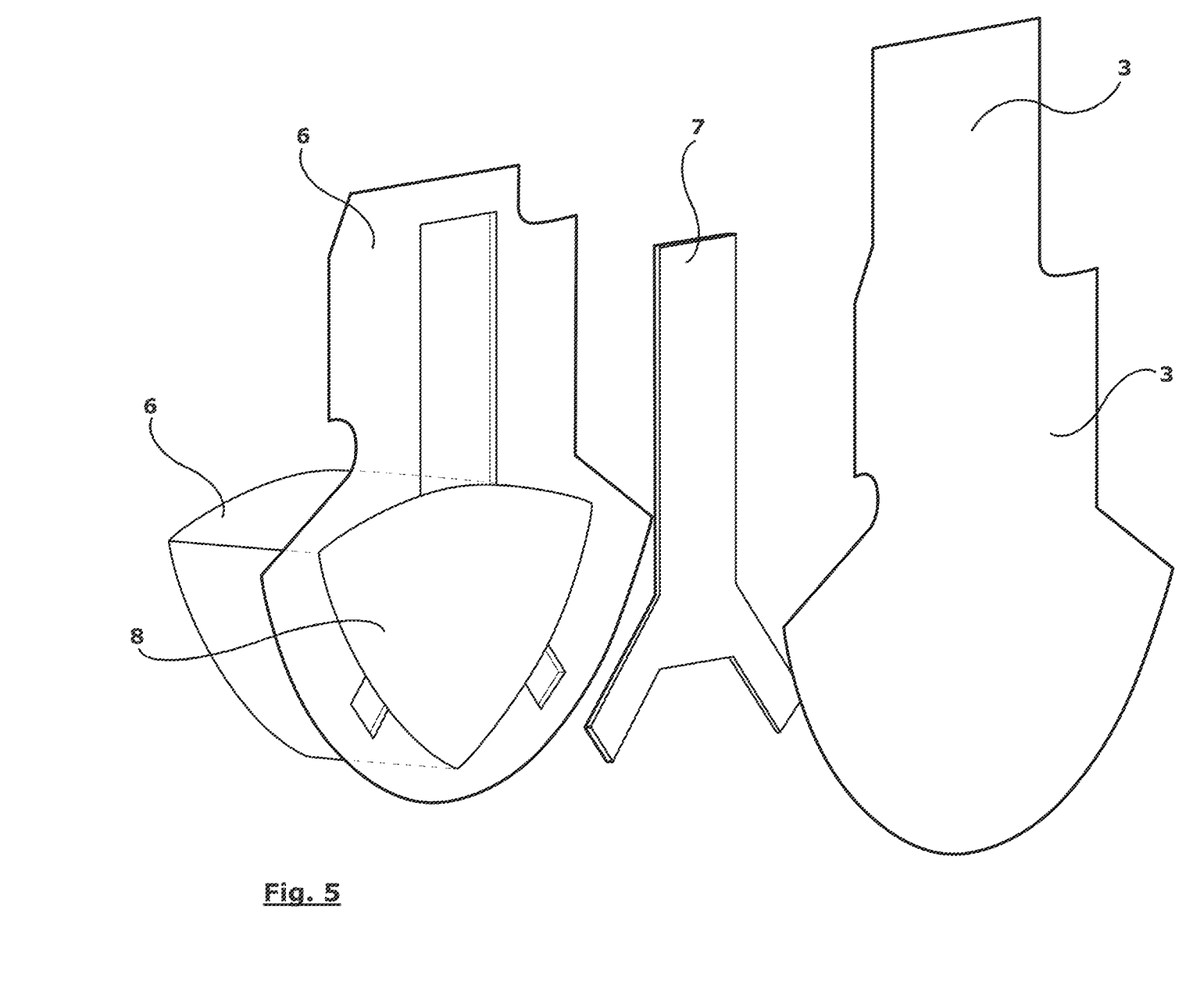
FIG. 5 is an exploded perspective view of a second embodiment of the diffuser of the present invention.
Figure 6:
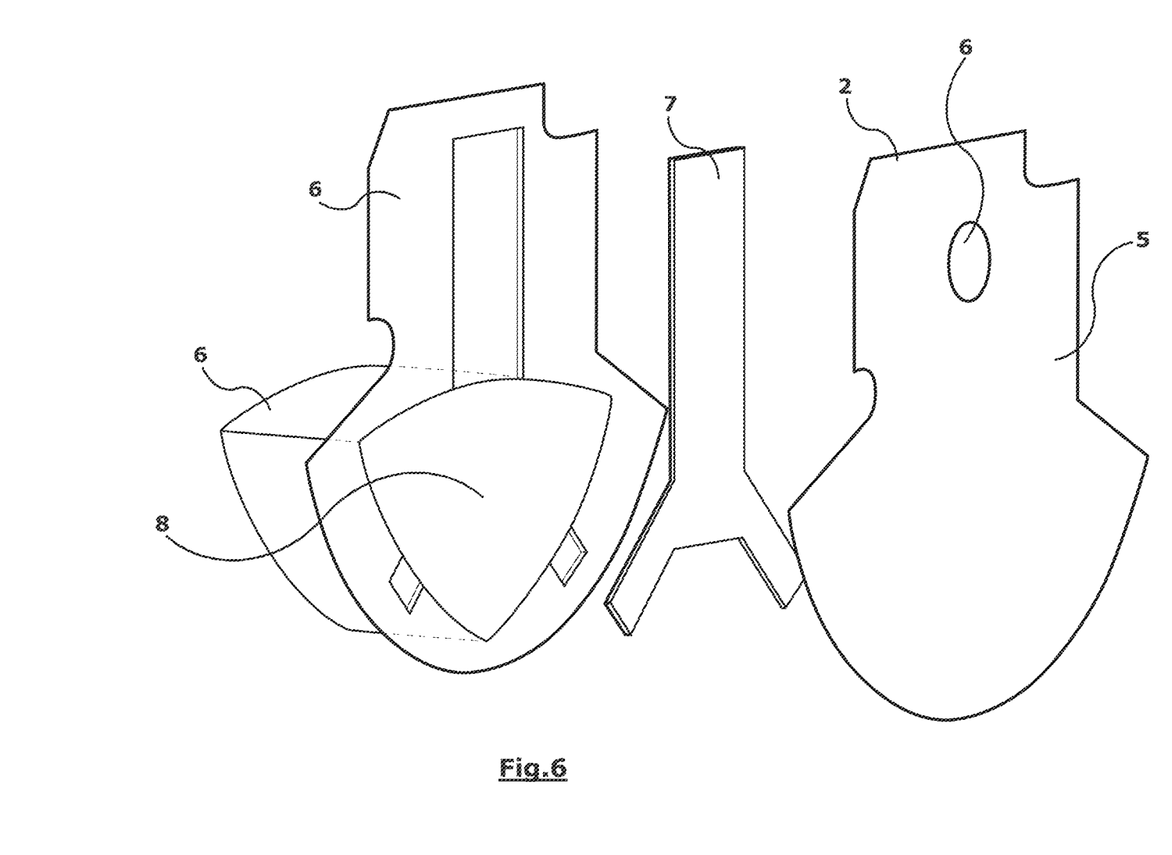
FIG. 6 is a view similar to FIG. 5, after the sealing film partial removal.

Example 2—Container of Active Liquid Agents with Wick (FIGS. 5-6)

The container 1 in this case consists of a sheet of PET/EVOH/PE, having a thickness of 450 microns, thermoformed so as to have a flat perimeter flange and a central cavity that comprises two different depth zones; more precisely, an area with greater depth of about 20 mm, for containing the active liquid agent 8, and an area elongating upward having a much lower depth of about 2 mm.

A porous cellulose element 7 having a Y-shape and thickness of about 2 mm, which acts as a wick, is disposed between the container 1 and the multilayer film 3, inhibiting a direct contact between said multilayer film 3 and the active liquid agent 8. The elongated portion of the wick 7 is disposed in the cavity of lesser depth of the thermoformed container 1, while the two diverging ends of the Y shape are placed in respective low-thickness cavities formed in the perimeter flange.

The multilayer film consists, as in the previous Example, of a PE inner sealing layer 2, a PP intermediate release layer 3b, an aluminium external barrier layer 3a and a further PET external protection layer.

The PE inner sealing layer 2 is cut according to a circular incision area, so as to create in the same—after peeling of the external barrier layer 3a and of the intermediate release layer 3b, by acting on tab 3'—a single circular orifice 6 of the diameter of 10 mm in an area facing the central part of the wick. Preferably, in the process of application of the multilayer film to the container 1, the edge of such circular orifice 6 is welded to the wick 7, so as to avoid any possible leaking of active liquid agent between the wick and the multilayer film.

The container thus formed can then be directly associated with a heating device to obtain the emanation of the active agent at a controlled temperature above room temperature.

Figure 7:
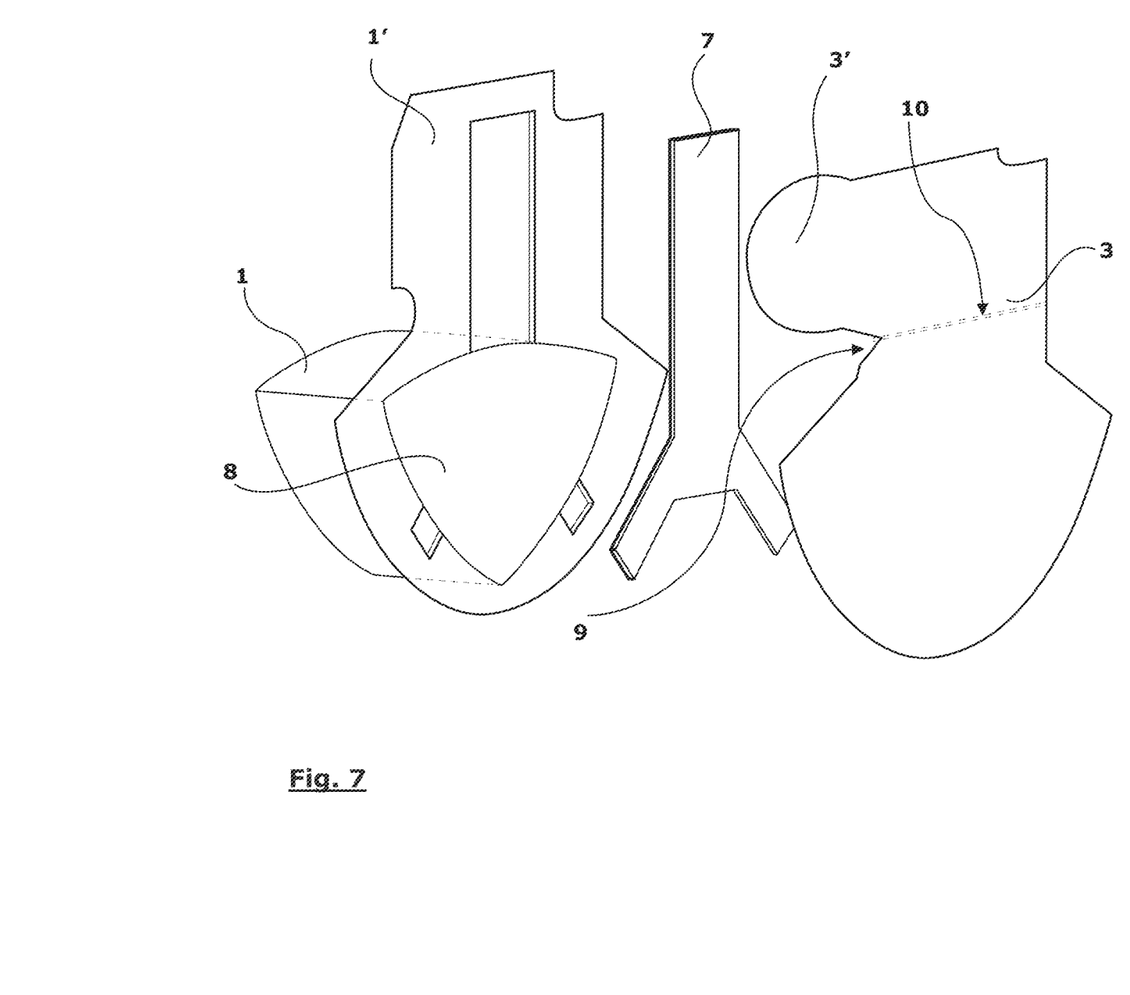
FIG. 7 is an exploded perspective view of a third embodiment of the diffuser of the present invention.
Figure 8:
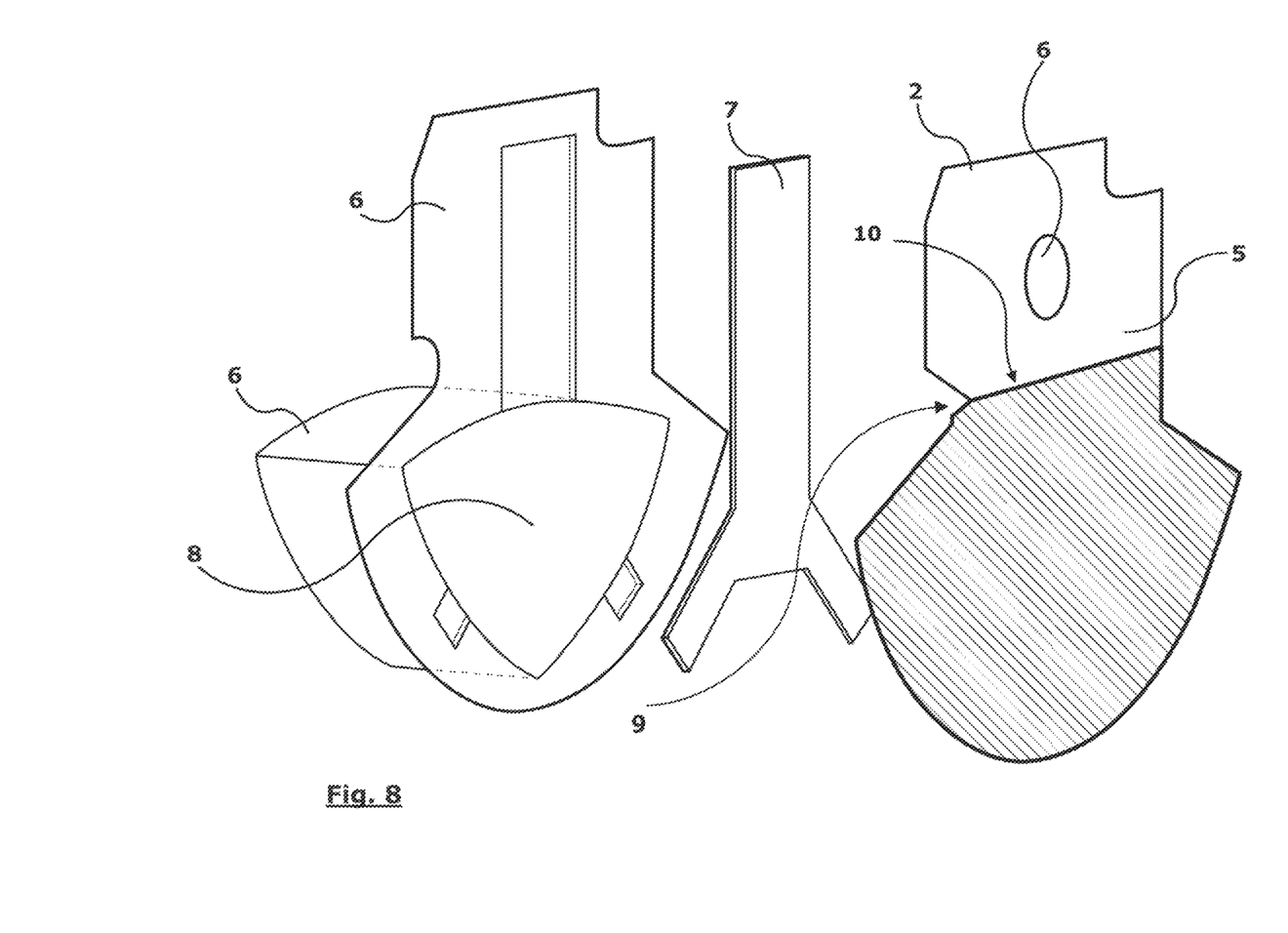
FIG. 8 is a view similar to FIG. 7, after the sealing film partial removal.

Example 3—Container of Active Liquid Agents with Wick (FIGS. 7-8)

A container 1 is formed in the same manner described in Example 2 and a similar wick 7 is disposed in the same. The multilayer film consists, as in the previous Example, of a PE inner sealing layer 2, a PP intermediate release layer 3b, an aluminium external barrier layer 3a and a further PET protection layer, in which a circular orifice 6 is cut as in Example 2.

Unlike the previous example, the PE inner sealing layer of the multilayer film is, however, permeable only to vapours of the active agent. In addition, a guide 9 and an incision line 10 are formed on the external barrier layer 3a in the manner described in detail in the Italian patent application no. 102015000022867, in the name of the same Applicant.

In this combined solution, when the user activates the device by means of peeling the external barrier layer 3a, the external barrier layer is removed only in its upper portion while it remains intact in the lower part which covers the portion of the active agent reservoir 8 having a greater depth.

Thanks to this construction, it is therefore possible to use the diffuser of the invention either in the same way described in the above-mentioned patent, i.e., by exploiting only the natural evaporation rate of the active substance, or by combining the diffuser with a heating device, to obtain an increased active agent emanation, through the wick 7 and the orifice 6.

It is understood, however, that the invention is not to be considered as limited by the particular arrangements illustrated above, which represent only exemplary implementations of the same, but different variants are possible, all within the reach of a person skilled in the art, without departing from the scope of the invention itself, as defined by the following claims.

The invention claimed is:

1. A diffuser of an active liquid agent, for the treatment of a gaseous or liquid environment, the diffuser comprising:
    a container of said active liquid agent, at least partly closed by a grid configured to retain in position said active liquid agent, said container and the grid being covered in advance of a first use of the diffuser by an external barrier film that is configured to be peeled off of the diffuser at the first use of the diffuser in order to make said grid operative to allow emission of the active liquid agent toward the gaseous or liquid environment, said grid and the external barrier film being formed as a single multilayer film comprising at least an external barrier layer and at least an inner sealing layer that forms said grid,
    wherein said external barrier layer and predefined incision portions of said inner sealing layer are configured to be simultaneously removed from the container such that the predefined incision portions of the inner sealing layer adhere to the external barrier layer and are not laterally connected to a remaining part of the inner sealing layer at the first use of the diffuser, wherein said active liquid agent is separated from said multilayer film by a porous solid support acting as a wick.

2. The diffuser as in claim 1, wherein said multilayer film further comprises an intermediate release layer between said external barrier layer and said inner sealing layer.

3. The diffuser as in claim 2, wherein a peripheral inner edge of the inner sealing layer of said multilayer film is thermally welded onto a flange edge of said container.

4. The diffuser as in claim 2, wherein said inner sealing layer is configured to maintain in the position the active liquid agent, the inner sealing layer being internally structured with the incision portions which run through an entire thickness of said inner sealing layer according to a predefined pattern, said external barrier layer is configured to prevent outward leaking of the active agent, and said intermediate release layer configured to facilitate detachment by peeling between said intermediate release layer and the inner sealing layer, when a sufficient traction effort is imparted to the external barrier layer.

5. The diffuser as in claim 4, wherein a peripheral inner edge of the inner sealing layer of said multilayer film is thermally welded onto a flange edge of said container.

6. The diffuser as in claim 4, wherein said inner sealing layer is a PE plastic material, said intermediate release layer is a PP plastic material, and said external barrier layer is aluminum.

7. The diffuser as in claim 6, wherein a peripheral inner edge of the inner sealing layer of said multilayer film is thermally welded onto a flange edge of said container.

8. The diffuser as in claim 1, wherein a peripheral inner edge of the inner sealing layer of said multilayer film is thermally welded onto a flange edge of said container.

9. The diffuser as in claim 1, wherein said inner sealing layer has an inner structure of incisions which extend at least across an entire depth thereof, according to one or more closed lines which delimit a perimeter of said removable incision portions, that are no longer laterally connected to the remaining part of said inner sealing layer.

10. The diffuser as in claim 9, wherein said removable incision portions of the inner sealing layer remaining adherent to said external barrier layer, leave corresponding cavities in said inner sealing layer, upon the removal of said external barrier layer.

11. The diffuser as in claim 1, wherein said active liquid agent is imbued in a solid or gel-like support.

12. The diffuser as in claim 1, wherein said inner sealing layer is permeable to the vapors of said active liquid agent.

13. The diffuser as in claim 1, wherein said inner sealing layer is welded to said porous solid support acting as the wick, in correspondence to edges of orifices formed in the inner sealing layer.

14. A manufacturing process of a diffuser as in claim 1, the process comprising:

forming said multilayer film, with at least the inner sealing layer and at least the external barrier layer;

cutting at least said inner sealing layer according to closed-perimeter incision lines which run through an entire thickness of said inner sealing layer, according to a predefined pattern which defines the removable incision portions that are no longer laterally connected with the remaining part of said inner sealing layer; and applying and accurately welding an inner edge of said multilayer film onto a flange edge of said container.

15. The process as in claim 14, wherein said incision lines extend at least partly into said intermediate release layer.

16. The process as in claim 14, wherein said incision lines are performed mechanically, with cutting blades at a controlled cutting depth.

17. The process as in claim 14, wherein said incision lines are performed thermo-mechanically, with thermal-action knives with controlled cutting depth.

18. The process as in claim 14, wherein said incision lines are performed with a laser cut, adjusting the cutting depth by controlling the applied power.

19. The process as in claim 14, further comprising disposing an intermediate release layer in between the inner sealing layer and the external barrier layer.

* * * * *